United States Patent [19]

Hayakawa

[11] 4,002,053
[45] Jan. 11, 1977

[54] METHOD AND APPARATUS FOR MEASURING DENSITY OF SUSPENSION

[75] Inventor: Noboru Hayakawa, Tokyo, Japan

[73] Assignee: Nishihara Environmental Sanitation Research Corporation Ltd., Japan

[22] Filed: Sept. 17, 1975

[21] Appl. No.: 614,434

[30] Foreign Application Priority Data

Sept. 20, 1974 Japan .............................. 49-108446

[52] U.S. Cl. .............................................. 73/32 R
[51] Int. Cl.² ........................................ G01N 9/24
[58] Field of Search ................................... 73/32 R

[56] References Cited

UNITED STATES PATENTS

| 3,229,503 | 1/1966 | Poole et al. | 73/32 R |
| 3,478,575 | 11/1969 | Meyer et al. | 73/32 R |
| 3,481,203 | 12/1969 | Ackerman et al. | 73/32 R X |

FOREIGN PATENTS OR APPLICATIONS

| 650,004 | 10/1962 | Canada | 73/32 R |
| 1,207,664 | 12/1965 | Germany | 73/32 R |
| 1,089,674 | 11/1967 | United Kingdom | 73/32 R |

Primary Examiner—James J. Gill
Attorney, Agent, or Firm—Bucknam and Archer

[57] ABSTRACT

Disclosed are a method and apparatus for measuring the density of a suspension wherein the suspension to be measured is first subjected to pressurization or depressurization in a closed container by means of a compressor or a vacuum pump to extinguish air bubbles and gas bubbles which would otherwise cause measurement error, and the measurement of the density of the suspension is then achieved with high exactitude in a bubble free state.

4 Claims, 6 Drawing Figures

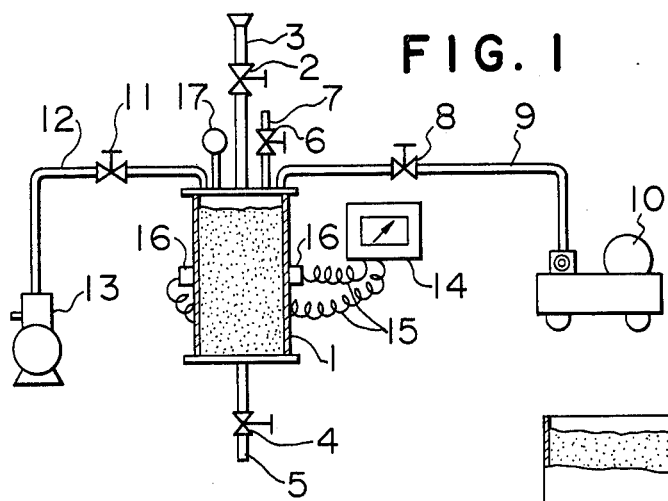
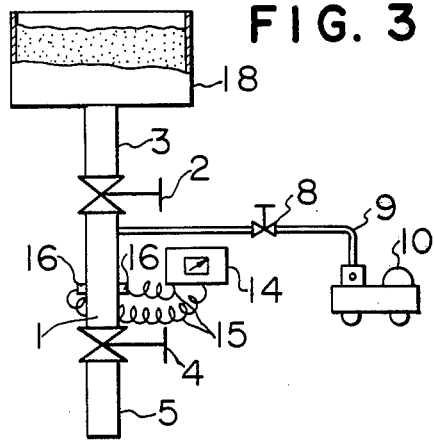
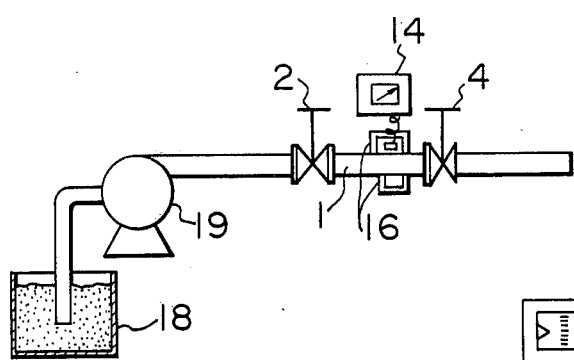
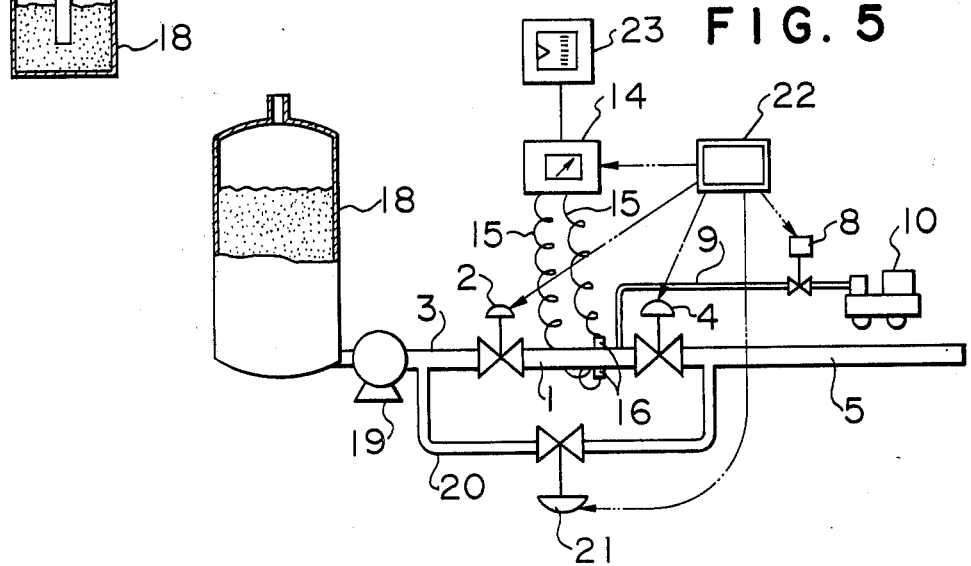

METHOD AND APPARATUS FOR MEASURING DENSITY OF SUSPENSION

BACKGROUND OF THE INVENTION

This invention relates to improvement in a method and apparatus for measuring the density of a suspension containing micro solid materials in suspensive state.

There are known such various methods for measuring the density of a suspension as the light method, the radiation and the ultrasonic wave method. However these conventional methods have a fatal limitation in that none is capable of exactly measuring the density of the suspension when air or gas bubbles are present in the suspension to be measured.

For example, in using the radiation method, the reading obtained is lower than real density owing to the existence of air bubbles. On the other hand, in using the light method or the ultrasonic wave method, the reading obtained in higher than the real density. Either way, a measurement error cannot be avoided and in extreme cases the error is so great as to make the measurement totally unreliable.

SUMMARY OF THE INVENTION

It is an object of this invention to provide a method and an apparatus for measuring the density of a suspension whereby it is possible to eliminate error and obtain an exact and rapid measurement by extinguishing the air bubbles and gas bubbles which would otherwise cause measurement error.

The method of measuring the density of a suspension of this invention is characterized in subjecting the suspension to be measured to pressurization or depressurization treatment to extinguish air and gas bubbles existing in the suspension and thereafter conducting the measurement under such bubble free condition.

The apparatus for measuring the density of a suspension comprises, in combination, means for retaining the suspension, hydraulic pressure changing means for pressurizing or depressurizing the suspension contained in said retaining means and means for measuring the suspension pressurized or depressurized by said hydraulic pressure changing means.

BRIEF DESCRIPTION OF THE DRAWINGS

FIG. 1 is a schematic diagram showing an embodiment of the apparatus of this invention for measuring the density of a suspension;

FIG. 3 through FIG. 5 are schematic diagrams showing other embodiment of the measuring apparatus.

DESCRIPTION OF THE PREFERRED EMBODIMENT

Figure 2:
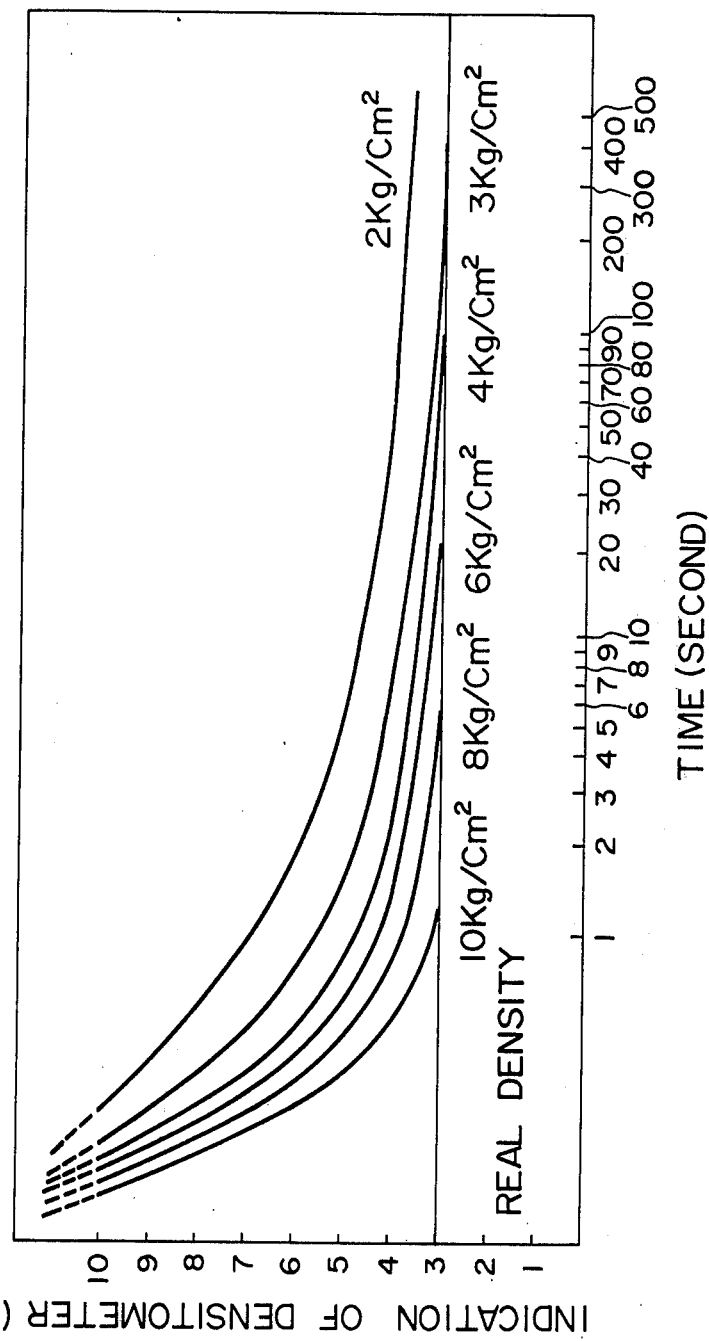
FIG. 2 is a graph representation showing measured values of the density of digested sludge.

Referring to the FIG. 1, 1 is a closed type tank for retaining the suspension to be measured, 2 is an inlet valve for introducing the suspension to the tank 1, 3 is an inlet pipe, 4 is an outlet valve, 5 is an outlet pipe, 6 is a pressure release valve opening into the atmosphere, 7 is a pressure release pipe, 8 is a pressurization valve, 9 is a pressurization pipe, 10 is an air compressor, 11 is a depressurization valve, 12 is a depressurization pipe, 13 is a vacuum pump, 14 is an ultrasonic wave type densitometer, 15 is detection cables, 16 is detection members and 17 is a pressure gauge.

Measurement using the apparatus shown in FIG. 1 is carried out as follows:

The inlet valve 2 is opened to introduce the suspension from the inlet pipe into the closed type tank 1 while the outlet valve 4 in the outlet pipe 5 is closed. The pressure valve 8 is then opened to introduce compressed air into the tank 1 from the air compressor 10 to thereby increase the hydraulic pressure of the suspension in the tank 1 and extinguish air and gas bubbles existing therein by causing them to disolve into the suspension.

The density of the suspension is then measured by the densitometer 14. As the measurement is conducted when the suspension is in a bubble free state, the readings obtained are highly accurate.

The graph in FIG. 2 shows the time interval required for the measured density reading to reach the real density value when the density of digested sludge obtained in sewege treatment and containing gas by its very nature was measured at various pressures using the apparatus shown in FIG. 1.

The reading of the densitometer (%) is plotted on the ordinate and the time in seconds after pressurization is plotted on the obscissa. The maximum reading of the densitometer used was 10% and the real density of the sludge sample was 3% (weight percent). As the sludge sample inherently contained gas and air bubbles, the needle of the ultrasonic wave type densitometer would have gone off scale if the measurement had been carried out without treatment according to this invention.

From the result of the measurement, it is seen that here is an interrelation between the pressure and the time required for the needle to reach the neighbourhood of the real density.

In a densitometer for practical industrial application, the shorter the interval between the pressurizing operation and extinguishment of the air and gas bubbles in the suspension, the more advantageous. Although this interval can be shortened by increasing the pressure applied to the suspension, the maximum pressure is limited by safety requirements. A safe and practical maximum is the 10 kg/cm$^2$ set by the Safety Provisions of the Ministry of Labor of Japan.

Although in the embodiment shown in FIG. 1, an air compressor is used as the hydraulic pressure changing device used to pressurize the suspension, any of various other means can be used instead so far as the required pressure is attained.

It is not necessary that the pressure changing device be separate from the tank 1. For example, tank 1 can be a cylinder having a piston which when actuated, provides the required pressure by decreasing volume of the cylinder. Or again, a device having a tank closed at one end and connected at the other end to a displacement pump can be used to pressurize the suspension. The densitometer is not restricted to the ultrasonic wave type but may be of light type, radiation type or other type.

With some types of suspensions, it is best to increase the pressure gradually, while with others more favorable results are obtained by rapidly increasing the pressure to the limit.

It was confirmed by experiment that the suspension which has once been sufficiently pressurized to eliminated bubbles will remain bubble free state long enough to conduct the density measurement (about 5 minutes) even after the pressure is removed so long as it is not subjected to heating or depressurization. Accordingly, the densitometer need not be located in the closed tank but can located in a non-pressurized container to which the suspension is transferred after pressurization.

Returning to FIG. 1, when the vacuum pump 13 is operated to reduce the hydraulic pressure of the suspension in the tank 1, bubbles in the suspension are expanded in volume and caused to float to the surface of the suspension where they disapear. Therefore, similarly to when the suspension is pressurized, a density measurement of high accuracy can be obtained. By combining the pressurizing operation and depressurizing operation, the bubble extinguishment effect can be even further enhanced. In an operating system the pressurization and depressurization methods are selectively applied as circumstances require.

FIG. 3 and FIG. 4 show apparatuses suitable for industrial application. In these drawings the same reference numerals are used to indicate parts which are identical with or similar to those of FIG. 1. In these apparatuses the part for retaining the suspension to be measured is a pipe portion 1 between the inlet pipe 3 and the outlet pipe 5. Numeral 18 indicates a suspension storage tank and numeral 19 indicates a displacement pump.

In the measuring system shown in FIG. 3, the suspension is introduced from the storage tank 18 into the pipe portion by opening the inlet valve 2 and closing the outlet valve 4 and then, the valve 2 is closed. The suspension is then pressurized to the required degree by the compressor 10. In using air compressor, the pressure applied to the suspension is maintained constant by, for example, a pressure switch or an automatical unloading device.

On the other hand, in the apparatus shown in FIG. 4 which employs a displacement compressor, the pressure is preferably controlled by a pressure switch or by controlling the running time of the pump by a timer or other means.

The ultrasonic wave type densitometer is used in the system shown in FIG. 3 and the radiation type densitometer is used in the system shown in FIG. 4. In either apparatus, it is advantageous to provide the densitometer at the part where the suspension is retained, because the measurement can be made free from external disturbance. After the measurement has been completed, the series of measuring operations is concluded by opening the outlet valve 4 and exhausting the measured suspension.

FIG. 5 shows an embodiment of a measuring system for conducting on-line measurement of the density of sludge being passed through a pipe under pressure in a waste water treatment process. The automatic valves 2 and 4 are respectively connected to supply side and drain side of the pipe portion 1 for retaining the sludge to be measured. The valves 2 and 4 are normally fully opened to allow the sludge to pass through the pipe portion 1.

Pipe 20 which is connected at one end to the inlet pipe 3 and at the other end to the outlet pipe 5 so as to bypass the valves 2 and 4, and the pipe portion 1 is provided with an automatic valve 21 which is normally kept fully closed so that the sludge flows only through the pipe 1. If the valve 21 is provided, the flow resistance of the pipe 20 can be made equal to or even smaller than that of the pipe 1. On the other hand, the valve 21 is not absolutely necessary if the diameter of the bypass pipe 20 is made somewhat smaller than that of the pipe 1 so that in normal operation the flow of the sludge through the bypass pipe is small.

The sludge thus passes mainly through the pipe portion 1 for retaining the sludge so that the sludge retained in the pipe portion 1 will reflect the moment to moment changes in density of the sludge passing through the system.

Upon command from the sequence circuit 22, the automatic valves 2 and 4 are fully closed and the automatic valve 21 is fully opened for a predetermined period of time. After the sludge sample has been retained by the closing of the valves 2 and 4, the pressurization valve 8 is opened to apply the necessary pressure to the sludge. Of course, in this case, it is convenient to prestart the air compressor 10 so that the required level of pressure is available when needed.

A timer in the sequence circuit 22 measures the time required for bubble extinguishment and after the passage of this time commands the densitometer 14 to begin the measurement. The measured value is memorized by a memory device 23 provided with a servomechanism. The memorized value is retained until it is replaced by the next value. During the measurement operation, the sludge passes through a bypass conduit 20 so that the process is not interrupted.

Figure 6:
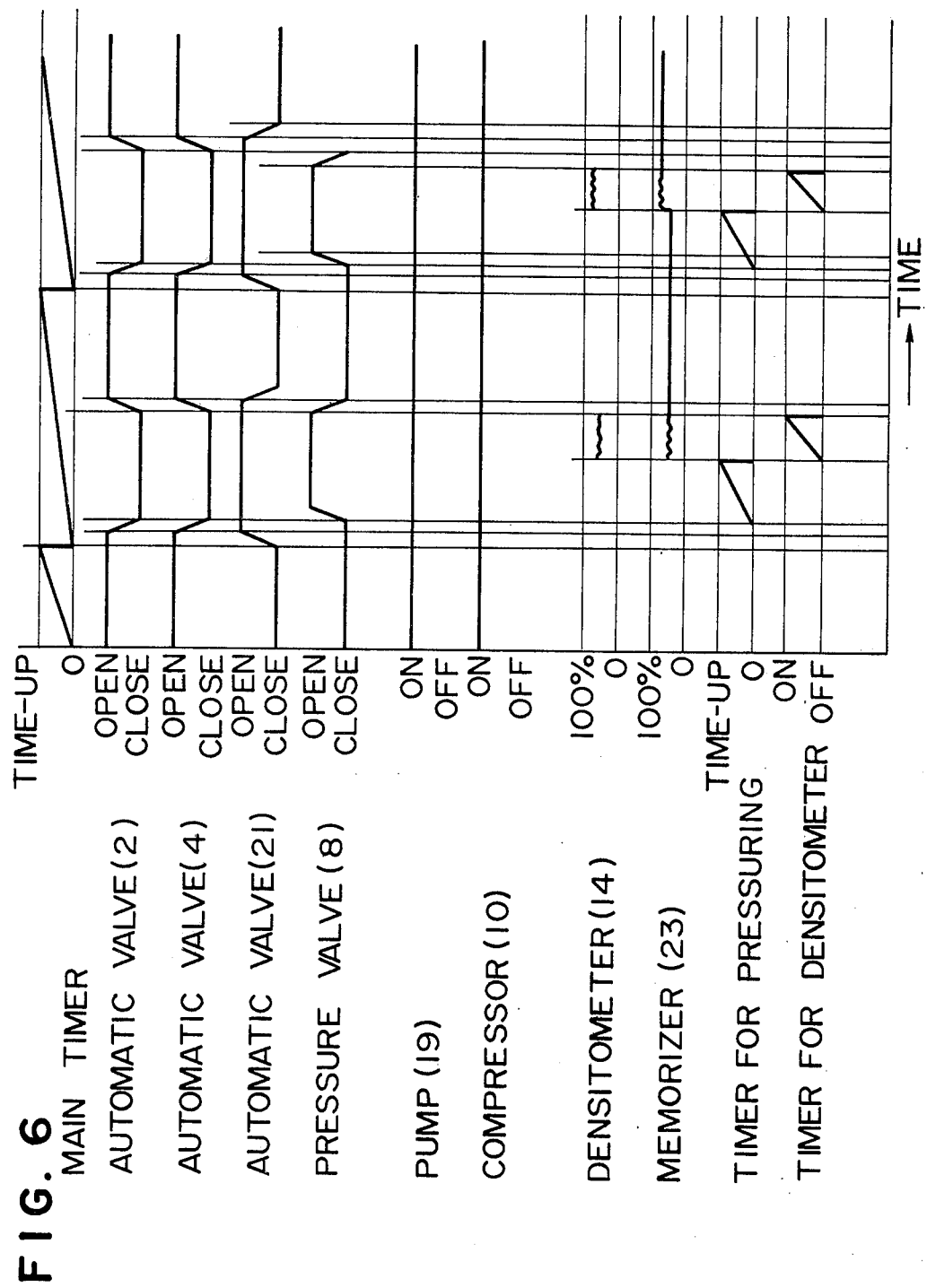
FIG. 6 is a time chart for the measuring system of this invention.

When the series of measurement operations is concluded, the automatic valves 2 and 4 are opened, the pressurization valve 8 and the valve 21 are closed, and the system returns to its initial condition. The time chart in FIG. 6 shows an example of these operations. The timer setting shown in this chart may freely changed so long as there is no interference with the measurement operation.

With the measurement system described above, it is possible to accomplish automatic measurement within the closed conduit without removing samples of the suspension therefrom. The system is thus appliable to a field wherein on-line density measurement has been considered very difficult, namely, to the on-line measurement of the density of suspensions including air and gas bubbles.

In summary, this invention relates to a system wherein the suspension to be measured is subjected to pressurization treatment, depressurization treatment or a combination of these treatments to thereby extinguish air and gas bubbles in the suspension which would otherwise cause the densitometer to register a measurement error. As the density of the suspension is measured in a bubble free state, the real density of suspensions including bubbles can be measured with high exactitude.

This invention therefore greatly contributes to expanding the fields in which density measurement can be accomplish and is extremely advantages for industrial application.

What is claimed is:

1. An apparatus for measuring the density of a suspension comprising a storage tank for the suspension; pipe means extending from the storage tank comprising an inlet pipe and an outlet pipe; an inlet valve and an outlet valve disposed on the pipe means in a spaced relation from each other to retain the suspension from the storage tank in a confined space in said pipe means when the inlet and outlet valves are in their closed position; a by-pass pipe by by-passing the inlet valve and the outlet valve, through which the suspension continuously fed from the storage tank flows when the suspension is confined in said pipe means between the inlet and outlet valves; means for changing the pressure of the confined suspension; means for measuring the density of the suspension, said means being mounted on the pipe means between the inlet and outlet valves; and a sequential circuit being adapted to control shut-off of the outlet valve and the inlet valve, and then to control operation of the pressure changing means to change the pressure of the confined suspension, and to control operation of the density measuring means by detecting the completion of the pressure change.

2. An apparatus for measuring the density of the suspension according to claim 1, which further comprises a third valve mounted on the by-pass pipe, said third valve being controlled by the sequential circuit so that, when the inlet and outlet valves are opened, the third valve is shut off and when the inlet and outlet valves are shut off, the third valve is opened.

3. An apparatus for measuring the density of the suspension according to claim 1, wherein the pressure changing means comprises a pressurizing device and a depressurizing device.

4. The apparatus according to claim 1 wherein the diameter of the by-pass is smaller than the diameter of said pipe means.

* * * * *